US009656070B2

(12) United States Patent
Gozani et al.

(10) Patent No.: US 9,656,070 B2
(45) Date of Patent: May 23, 2017

(54) APPARATUS AND METHOD FOR RELIEVING PAIN USING TRANSCUTANEOUS ELECTRICAL NERVE STIMULATION

(71) Applicant: NeuroMetrix, Inc., Waltham, MA (US)

(72) Inventors: Shai N. Gozani, Brookline, MA (US); Xuan Kong, Acton, MA (US); Andres Aguirre, Belmont, MA (US); Glenn Herb, Weston, MA (US); Marc Cryan, Maynard, MA (US); Michael Williams, Melrose, MA (US)

(73) Assignee: NeuroMetrix, Inc., Waltham, MA (US)

( * ) Notice: Subject to any disclaimer, the term of this patent is extended or adjusted under 35 U.S.C. 154(b) by 0 days.

(21) Appl. No.: 14/610,757

(22) Filed: Jan. 30, 2015

(65) Prior Publication Data
US 2015/0148865 A1   May 28, 2015

Related U.S. Application Data

(63) Continuation of application No. 13/678,221, filed on Nov. 15, 2012, now Pat. No. 8,948,876.
(Continued)

(51) Int. Cl.
*A61N 1/36* (2006.01)
*A61N 1/04* (2006.01)
(Continued)

(52) U.S. Cl.
CPC ....... *A61N 1/36021* (2013.01); *A61N 1/0456* (2013.01); *A61N 1/0476* (2013.01);
(Continued)

(58) Field of Classification Search
CPC ............ A61N 1/36021; A61N 1/36014; A61N 1/0456; A61N 1/0476; A61N 1/0492; A61N 1/321; A61N 1/37247
See application file for complete search history.

(56) References Cited

U.S. PATENT DOCUMENTS

| 4,503,863 A | 3/1985 | Katims |
| 4,605,010 A | 8/1986 | McEwen |

(Continued)

FOREIGN PATENT DOCUMENTS

| WO | WO 99/64105 | 12/1999 |
| WO | WO 2008/088985 | 7/2008 |

OTHER PUBLICATIONS

Bjordal JM et al., Transcutaneous electrical nerve stimulation (TENS) can reduce postoperative analgesic consumption. A meta-analysis with assessment of optimal treatment parameters for postoperative pain, European Journal of Pain, 2003, vol. 7(2): 181-188.
(Continued)

*Primary Examiner* — Catherine Voorhees
(74) *Attorney, Agent, or Firm* — Pandiscio & Pandiscio

(57) ABSTRACT

Apparatus for transcutaneous electrical nerve stimulation in humans, the apparatus comprising: a housing; stimulation means mounted within the housing for electrically stimulating nerves; an electrode array releasably mounted to the housing and connectable to the stimulation means, the electrode array comprising a plurality of electrodes for electrical stimulation of nerves; control means mounted to the housing and electrically connected to the stimulation means for controlling at least one characteristic of the stimulation means; monitoring means mounted to the housing and electrically connected to the stimulation means for monitoring at least one characteristic of the stimulation means; user interface means mounted to the housing and electrically connected to the control means for controlling the stimulation means; display means mounted to the housing and electrically connected to the control means and the monitoring means for displaying the status of the stimulations means; and a strap attached to the housing; wherein the strap is configured to hold the housing, stimulation means
(Continued)

and electrode array at a specific anatomical location to treat pain.

63 Claims, 9 Drawing Sheets

Related U.S. Application Data

(60) Provisional application No. 61/560,029, filed on Nov. 15, 2011, provisional application No. 61/657,382, filed on Jun. 8, 2012.

(51) Int. Cl.
*A61N 1/32* (2006.01)
*A61N 1/372* (2006.01)

(52) U.S. Cl.
CPC ........... *A61N 1/0492* (2013.01); *A61N 1/321* (2013.01); *A61N 1/36014* (2013.01); *A61N 1/37247* (2013.01)

(56) References Cited

U.S. PATENT DOCUMENTS

| | | | |
|---|---|---|---|
| 4,738,250 A | 4/1988 | Fulkerson et al. | |
| 5,063,929 A | 11/1991 | Bartelt et al. | |
| 5,169,384 A | 12/1992 | Bosniak et al. | |
| 5,350,414 A | 9/1994 | Kolen | |
| 5,487,759 A * | 1/1996 | Bastyr | A61N 1/36021 607/115 |
| 5,562,718 A * | 10/1996 | Palermo | A61N 1/36021 607/46 |
| 5,806,522 A | 9/1998 | Katims | |
| 6,161,044 A * | 12/2000 | Silverstone | A61N 1/36025 607/45 |
| 6,266,558 B1 | 7/2001 | Gozani et al. | |
| 6,430,450 B1 | 8/2002 | Bach-y-Rita et al. | |
| 6,456,884 B1 * | 9/2002 | Kenney | A61F 5/0111 607/115 |
| 6,662,051 B1 | 12/2003 | Eraker et al. | |
| 7,668,598 B2 | 2/2010 | Herregraven et al. | |
| 7,720,548 B2 | 5/2010 | King | |
| 7,725,193 B1 * | 5/2010 | Chu | A61N 1/36021 607/48 |
| 8,131,374 B2 | 3/2012 | Moore et al. | |
| 2003/0074037 A1 * | 4/2003 | Moore | A61N 1/36021 607/63 |
| 2003/0114892 A1 | 6/2003 | Nathan et al. | |
| 2003/0208246 A1 | 11/2003 | Kotlik et al. | |
| 2005/0059903 A1 | 3/2005 | Izumi | |
| 2006/0085049 A1 | 4/2006 | Cory et al. | |
| 2006/0095088 A1 * | 5/2006 | De Ridder | A61N 1/3605 607/48 |
| 2006/0173507 A1 | 8/2006 | Mrva et al. | |
| 2007/0276449 A1 * | 11/2007 | Gunter | A61N 1/36021 607/46 |
| 2008/0077192 A1 * | 3/2008 | Harry | A61H 23/0263 607/48 |
| 2008/0146980 A1 | 6/2008 | Rousso et al. | |
| 2008/0147146 A1 | 6/2008 | Wahlgren et al. | |
| 2009/0030476 A1 | 1/2009 | Hargrove | |
| 2009/0131993 A1 | 5/2009 | Rousso et al. | |
| 2009/0240303 A1 | 9/2009 | Wahlstrand et al. | |
| 2009/0264789 A1 | 10/2009 | Molnar et al. | |
| 2009/0270947 A1 * | 10/2009 | Stone | A61N 1/0534 607/59 |
| 2009/0326604 A1 * | 12/2009 | Tyler | A61B 5/0492 607/45 |
| 2010/0042180 A1 * | 2/2010 | Mueller | A61N 1/0456 607/46 |
| 2010/0114257 A1 | 5/2010 | Torgerson | |
| 2010/0198124 A1 * | 8/2010 | Bhugra | A61B 5/0205 602/5 |
| 2011/0224665 A1 | 9/2011 | Crosby et al. | |
| 2011/0257468 A1 | 10/2011 | Oser et al. | |
| 2011/0264171 A1 * | 10/2011 | Torgerson | A61N 1/36 607/59 |
| 2011/0276107 A1 | 11/2011 | Simon et al. | |
| 2012/0010680 A1 * | 1/2012 | Wei | A61N 1/36007 607/40 |
| 2013/0096641 A1 * | 4/2013 | Strother | A61N 1/36021 607/46 |

OTHER PUBLICATIONS

Bloodworth DM et al , Comparison of stochastic vs. conventional transcutaneous electrical stimulation for pain modulation in patients with electromyographically documented radiculopathy, American Journal of Physical Medicine & Rehabilaiion, 2004, vol. 83(6): 5584-591.

Chandran P et al., Development of opioid tolerance with repeated transcutaneous electrical nerve stimulation administration, Pain, 2003, vol. 102: 195-201.

Chen CC et al., A comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.

Chen CC et al., An investigation into the effects of frequency-modulated transcutaneous electrical nerve stimulation (TENS) on experimentally-induced pressure pain in healthy human participants, The Journal of Pain, 2009; vol. 10(10): 1029-1037.

Chen CC et al., Differential frequency effects of strong nonpainful transcutaneous electrical nerve stimulation on experimentally induced ischemic pain in healthy human participants. The Clinical Journal of Pain, 2011, vol. 27(5): 434-441.

Chen CC et al., Does the pulse frequency of transcutaneous electrical nerve stimulation (TENS) influence hypoalgesia? A systemic review of studies using experimental pain and healthy human participants, Physiotherapy, 2008, vol. 94: 11-20.

Claydon LS et al., Dose-specific effects of transcutaneous electrical nerve stimulation on experimental pain, Clinical Journal of Pain, 2011, vol. 27(7) 635-647.

Crijccu G. et al., EFNS guidelines on neurostimulation therapy for neuropathic pain, European Journal of Neurology, 2007, vol. 14: 952-970.

Davies Hto et al., Diminishing returns or appropriate treatment strategy?—an analysis of short-term outcomes after pain clinic treatment, Pain, 1997, vol. 70: 203-208.

Desantana JM et al., Effectiveness of transcutaneous electrical nerve stimulation for treatment of hyperalgesia and pain, Curr Rheumatol Rep. 2008, vol. 10(6): 492-499.

Dubinsky RM et al.. Assessment: Efficacy of transcutaneous electric nerve stimulation in the treatment of pain in neurologic disorders (an evidence-based review): Report of the therapeutics and technology assessment subcommittee of the american academy of neurology, Neurology, 2010, vol. 74: 173-176.

Fary Re et al., Monophasic electrical stimulation produces high rates of adverse skin reactions in healthy subjects; Physiotherapy Theory and Practice, 2011, vol. 27(3): 246-251.

Garrison DW et al., Decreased activity of spontaneous and noxiously evoked dorsal horn cells during transcutaneous electrical nerve stimulation (TENS), Pain, 1991, vol. 58, 309-315.

Jelinek HF et al., Electric pulse frequency and magnitude of perceived sensation during electrocuteneous forearm stimulation, Arch Phys Med Rehabil, 2010, vol. 91: 1372-1382.

Jin DM et al., Effect of transcutaneous electrical nerve stimulation on symptometic diabetic peripheral neuropathy: a meta-analysis of randomized controlled trials. Diabetes Research and Clinical Practice. 2010. vol. 89: 10-15.

Johnson Mi et al., An in-depth study of long-term users of transcutaneous electrical nerve stimulation (TENS), Implications for clinical use of TENS, Pain, 1991, vol. 44: 221-229.

Johnson Mi et al., Analgesic effects of different frequencies of transcutaneous electrical nerve stimulation on cold-induced pain in normal subjects, Pain, 1989, vol. 39: 231-236.

(56) References Cited

OTHER PUBLICATIONS

Johnson Mi et al, Transcutaneous Electrical Nerve Stimulation (TENS) and TENS-like devices: do they provide pain relief?, Pain Reviews, 2001, vol. 8: 7-44.
Johnson Mi et al., Transcutaneous electrical nerve stimulation for the management of painful conditions: focus on neuropathic pain, Expert Review of Neurotherapeutics, 2011, vol. 11(5) 735-753.
Kantor G et al, The effects of selected stimulus waveforms on pulse and phase characteristics at sensory and motor thresholds, Physical Therapy, 1994, vol. 74(10): 951-962.
Law PPW et al., Optimal stimulation frequency of transcutaneous electrical nerve stimulation on people with knee osteoarthritis, J Rehabil Med, 2004, vol. 36: 220-225.
Leonard G et al., Deciphering the rote of endogenous oploids in high-frequency TENS using low and high doses of naloxone, Pain, 2010, vol. 151: 215-219.
Levy et al., A comparison of two methods for measuring thermal thresholds in diabetic neuropathy, Journal of Neurology. Neurosurgery, and Psychiatry, 1989, vol. 52: 1072-1077.
Melzack R et al., Pain mechanisms: A New Theory, Science, 1965, vol. 150(3699): 971-979.
Moran F et al., Hypoalgesia in response to transcutaneous electrical nerve stimulation: (TENS) depends on stimulation intensity, The Journal of Pain, 2011, vol. 12(8); 929-035.
Pantaleao MA et al., Adjusting pulse amplitude during transcutaneous electrical nerve stimulation (TENS) application produces greater hypoalgesia, The Journal of Pain, 2011, vol. 12(5): 581-590.
Pieber K et al., Electrotherapy for the treatment of painful diabetic peripheral neuropathy: a review, Journal of Rehabilitation Medicine, 2010, vol. 42: 289-295.

\* cited by examiner

APPARATUS AND METHOD FOR RELIEVING PAIN USING TRANSCUTANEOUS ELECTRICAL NERVE STIMULATION

REFERENCE TO PRIOR PATENT APPLICATIONS

This patent application is a continuation of pending prior U.S. patent application Ser. No. 13/678,221, filed Nov. 15, 2012 by NeuroMetrix, Inc. and Shai N. Gozani et al. for APPARATUS AND METHOD FOR RELIEVING PAIN USING TRANSCUTANEOUS ELECTRICAL NERVE STIMULATION, which in turn claims benefit of (i) prior U.S. Provisional Patent Application Ser. No. 61/560,029, filed Nov. 15, 2011 by Shai N. Gozani for SENSUS OPERATING MODEL; and (ii) prior U.S. Provisional Patent Application Ser. No. 61/657,382, filed Jun. 8, 2012 by Shai N. Gozani et al. for APPARATUS AND METHOD FOR RELIEVING PAIN USING TRANSCUTANEOUS ELECTRICAL NERVE STIMULATION.

The three (3) above-identified patent applications are hereby incorporated herein by reference.

FIELD OF THE INVENTION

This invention relates generally to Transcutaneous Electrical Nerve Stimulation (TENS) devices that deliver electrical currents across the intact skin of a patient via electrodes so as to provide symptomatic relief of chronic pain, and more particularly to the use of TENS devices to provide symptomatic relief of painful diabetic neuropathy.

BACKGROUND OF THE INVENTION

Diabetic peripheral neuropathy (DPN) is the most common chronic complication of diabetes mellitus, which affects about 25 million people in the United States and over 300 million people worldwide. DPN affects the peripheral nerves, mostly in the feet and lower legs. DPN may lead to a loss of sensation that may trigger foot ulcers requiring amputation. DPN may also lead to severe and debilitating neuropathic pain.

Pain due to DPN is called painful diabetic neuropathy (PDN). PDN affects about 50% of people with DPN, and 10-20% of all people with diabetes. PDN is generally treated pharmacologically using drugs that are typically anti-depressants or anti-epileptics. These drugs may be difficult to dose and may have substantial side effects in many people. As a result, people with diabetes and PDN are often undertreated, and as many as 50% of people with PDN may not be receiving any anti-pain therapy. Thus there is a clear need for additional analgesic options for the management of PDN.

Transcutaneous Electrical Nerve Stimulation (TENS) devices apply electrical currents to a particular area of the human body in order to suppress acute and chronic pain. Although not widely used in the management of PDN, recent evidence suggests that TENS should be considered as an adjunctive or primary therapy for patients with PDN.

The most common form of TENS is called conventional TENS. In conventional TENS, electrodes are placed on the skin within, adjacent to, or proximal to, the area of pain. Electrical stimulation is then delivered to the patient through the electrodes, with the electrical stimulation being in the form of low intensity (typically less than 50-60 mA), short duration (typically 50-200 μsec) pulses at frequencies typically between about 10 and 200 Hz.

The physiological principle underlying TENS is that excitation of Aβ sensory nerve fibers, primarily the deep tissue afferents, blocks transmission of pain signals to the brain. The most commonly cited mechanism of action is the "gate theory of pain" originally proposed by Melzack and Wall in 1965 (Melzack R, Wall P D. Pain mechanisms: a new theory. *Science*. 1965; 150:971-979). In recent years, the molecular mechanisms underlying TENS analgesia have been investigated. It has been determined that pain signals are blocked by inhibition of nociceptive neurons in the spinal cord dorsal horn (DeSantana J M, Walsh D M, Vance C, Rakel B A, Sluka K A. Effectiveness of transcutaneous electrical nerve stimulation for treatment of hyperalgesia and pain. Curr Rheumatol Rep. 2008; 10(6):492-499). This process is facilitated by descending signals from the periaqueductal gray (PAG) and the rostroventral medial medulla (RVM). There is also evidence that pain signals are interrupted in the peripheral nervous system. Sensory afferent stimulation causes release of endogenous opioids that inhibit pain through activation of δ-opioid receptors. These receptors are located throughout the nervous system, including the dorsal horn of the spinal cord. Opioid receptors are G-protein coupled receptors whose activation decreases neuronal activity, such as through ion channel regulation Like the morphine sensitive μ-opioid receptor, the δ-opioid receptor induces analgesia, however, the two receptor subtypes have a different neuroanatomical distribution and abuse potential. TENS also increases the extracellular concentration of the inhibitory neurotransmitter GABA and decreases the concentration of the excitatory neurotransmitters glutamate and aspartate in the spinal cord dorsal horn.

In a conventional TENS device, an electrical circuit generates stimulation pulses with specified characteristics. The pulse waveform specifications include intensity (mA), duration (μsec) and shape (typically monophasic or biphasic). The pulse pattern specifications include frequency (Hz) and length of the stimulation session (minutes). One or more pairs of electrodes, placed on the patient's skin, transduce the electrical pulses and thereby stimulate underlying nerves. By varying the intensity of the stimulation pulses and, to a lesser degree, the frequency of the stimulation pulses, the clinical benefit of TENS can be optimized.

There is evidence to suggest that a major barrier to the effective use of TENS therapy is the disproportionate amount of effort needed to regularly apply TENS relative to the amount of pain relief achieved. More particularly, most TENS devices are designed for general purpose use, i.e., to relieve pain originating from various sources and at various anatomical locations. This necessitates a TENS system with multiple discrete components. For example, the TENS electrodes and the TENS stimulator are typically connected to one another through long lead wires that may be difficult for patients to manage, and may cause embarrassment for the patient if externally visible. The electrodes themselves are typically generic in form and function, which places the onus on the patient to position the electrodes in a physiologically and clinically optimal arrangement. Because of these issues, general purpose TENS devices typically require extensive patient training and supervision by medical staff, and even with this training, patients are likely to forget key steps in the proper use of TENS devices. Bastyr et al. (U.S. Pat. No. 5,487,759) attempted to overcome some of these limitations by disclosing a stimulator used in conjunction with a support device, such as an orthopedic brace, with the support device providing mechanical and electrical connections between the stimulator and electrodes. Nevertheless, there remains a need for TENS devices that are uniquely designed for specific clinical indications, and which therefore render the use of TENS in those applications straightforward, with minimal if any medical support.

To achieve maximum pain relief (i.e., hypoalgesia), TENS needs to be delivered at an adequate stimulation intensity (Moran F, Leonard T, Hawthorne S, et al. Hypoalgesia in response to transcutaneous electrical nerve stimulation (TENS) depends on stimulation intensity. *J Pain.* 12:929-935). Intensities below the threshold of sensation are not clinically effective. The optimal therapeutic intensity is often described as one that is "strong but not painful". Most TENS devices rely on the patient to set the stimulation intensity, usually through a manual intensity control consisting of an analog intensity knob or digital intensity control push buttons. In either case, the patient must manually increase the intensity of the stimulation to what they believe to be a therapeutic level. Therefore, a major limitation of current TENS devices is that it may be difficult for many patients to determine an appropriate therapeutic stimulation intensity. As a result, the patients will either require substantial support from medical staff or they may fail to get pain relief due to an inadequate stimulation level. In an attempt to improve the likelihood of delivering an appropriate therapeutic stimulation, some TENS devices allow healthcare professionals to pre-program a target stimulation level. For example, Bartelt et al. (U.S. Pat. No. 5,063,929) disclosed a TENS device that gradually and automatically increases stimulation intensity to a programmed target level. However, even when a healthcare professional programs the target stimulation level, that level may not suffice after repeated use of the TENS device due to changes in the patient's pain and physiology. In an attempt to overcome some of these issues and automate stimulation intensity control, King et al. (U.S. Pat. No. 7,720,548) proposed a method of regulating stimulation parameters, such as stimulus intensity, based on an electrical impedance signal. However, the clinical usefulness of this method is unclear as the linkage between impedance and therapeutic stimulation intensity is unproven. For the reasons outlined above, current TENS devices suffer from significant limitations with respect to ensuring that the stimulation intensity is within the therapeutic range.

Thus there is a need for a new and improved TENS device which addresses the issues associated with prior art TENS devices.

SUMMARY OF THE INVENTION

The present invention comprises a novel TENS device which, in its preferred embodiment, comprises a stimulator designed to be placed on the patient's upper calf and a pre-configured electrode array designed to provide circumferential stimulation at the area of the upper calf. A key feature of the present invention is that the TENS device and its associated electrode array are designed for easy, rapid, and clinically valid placement of the electrode array by a patient seeking pain relief in the feet and/or lower legs. In a preferred embodiment, the present invention is used for the symptomatic treatment of chronic pain caused by PDN. Furthermore, the present invention is designed to maximize effectiveness and usability, and to minimize interference with the patient's normal daily activities.

With a TENS device, the most important stimulation parameter is the intensity of the stimulation, which must be in the therapeutic range to maximize pain relief. The present invention provides a novel method for determining the stimulation intensity so as to maximize the probability that the stimulation intensity is in the therapeutic range. In a preferred embodiment of the present invention, the patient identifies their sensation threshold and then the therapeutic intensity is estimated from the identified sensational threshold. The patient also has the option of making further refinements in the stimulation intensity.

Habituation refers to a decrease in sensory perception of a stimulus after prolonged presentation of the stimulus. In a preferred embodiment of the present invention, in order to overcome habituation, the stimulation intensity is designed to gradually increase throughout the entire therapy session, in contrast to prior art practices of requiring the patient to manually increase intensity periodically during the therapy session. The present invention also learns the manner and frequency of the manual adjustment of the desired stimulation intensity so as to customize the parameter sets that modify stimulation in order to combat habituation.

In one preferred form of the present invention, there is provided apparatus for transcutaneous electrical nerve stimulation in humans, the apparatus comprising:

a housing;

stimulation means mounted within the housing for electrically stimulating nerves;

an electrode array releasably mounted to the housing and connectable to the stimulation means, the electrode array comprising a plurality of electrodes for electrical stimulation of nerves;

control means mounted to the housing and electrically connected to the stimulation means for controlling at least one characteristic of the stimulation means;

monitoring means mounted to the housing and electrically connected to the stimulation means for monitoring at least one characteristic of the stimulation means;

user interface means mounted to the housing and electrically connected to the control means for controlling the stimulation means;

display means mounted to the housing and electrically connected to the control means and the monitoring means for displaying the status of the stimulations means; and a strap attached to the housing;

wherein the strap is configured to hold the housing, stimulation means and electrode array at a specific anatomical location to treat pain.

In another preferred form of the present invention, there is provided apparatus for providing transcutaneous electrical nerve stimulation to a patient, the apparatus comprising:

a housing;

stimulation means mounted within the housing for generating electrical pulses;

an electrode array releasably mounted to the housing and connectable to the stimulation means, the electrode array comprising a plurality of electrodes for applying the electrical pulse generated by the stimulation means to the skin of a patient; and a strap attached to the housing;

wherein the strap is configured to hold the electrode array against the skin of the patient so as to treat pain when the stimulation means generates electrical pulses.

In another preferred form of the present invention, there is provided electrode array for transcutaneous electrical nerve stimulation in humans, the electrode array comprising:

a substrate;

at least one electrode mounted to the substrate representing a cathode;

at least one electrode mounted to the substrate representing an anode;

connection means for connecting the electrodes representing the cathode and anode to electrical stimulation means for electrically stimulating nerves;

wherein the substrate and the electrodes representing the cathode and anode are designed to provide electrical stimulation at a specific anatomical location and where a minimum distance between electrodes representing the cathode and anode is maintained.

In another preferred form of the present invention, there is provided a method for determining a therapeutic stimulation intensity for transcutaneous electrical nerve stimulation in humans, the method comprising the steps of:

automatically increasing the stimulation intensity from a first stimulation intensity;

identifying at least one electrotactile perception threshold; and calculating a therapeutic stimulation intensity from said at least one electrotactile perception threshold.

In another preferred form of the present invention, there is provided a method for determining a therapeutic stimulation intensity for transcutaneous electrical nerve stimulation in a patient, the method comprising the steps of:

applying electrical stimulation to the patient at a first stimulation intensity;

automatically increasing the intensity of the electrical stimulation applied to the patient from the first stimulation intensity to a second intensity at which the electrotactile sensation threshold is identified; and calculating a therapeutic stimulation intensity from said second intensity level.

In another preferred form of the present invention, there is provided a method for treating pain in a patient using transcutaneous electrical nerve stimulation, the method comprising the steps of:

automatically determining a therapeutic stimulation intensity;

initiating electrical stimulation at the therapeutic stimulation intensity;

adjusting the therapeutic stimulation intensity under patient control;

automatically increasing the therapeutic stimulation intensity at a pre-determined rate; and continuing electrical stimulation for a period of time.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE INVENTION

Figure 1:
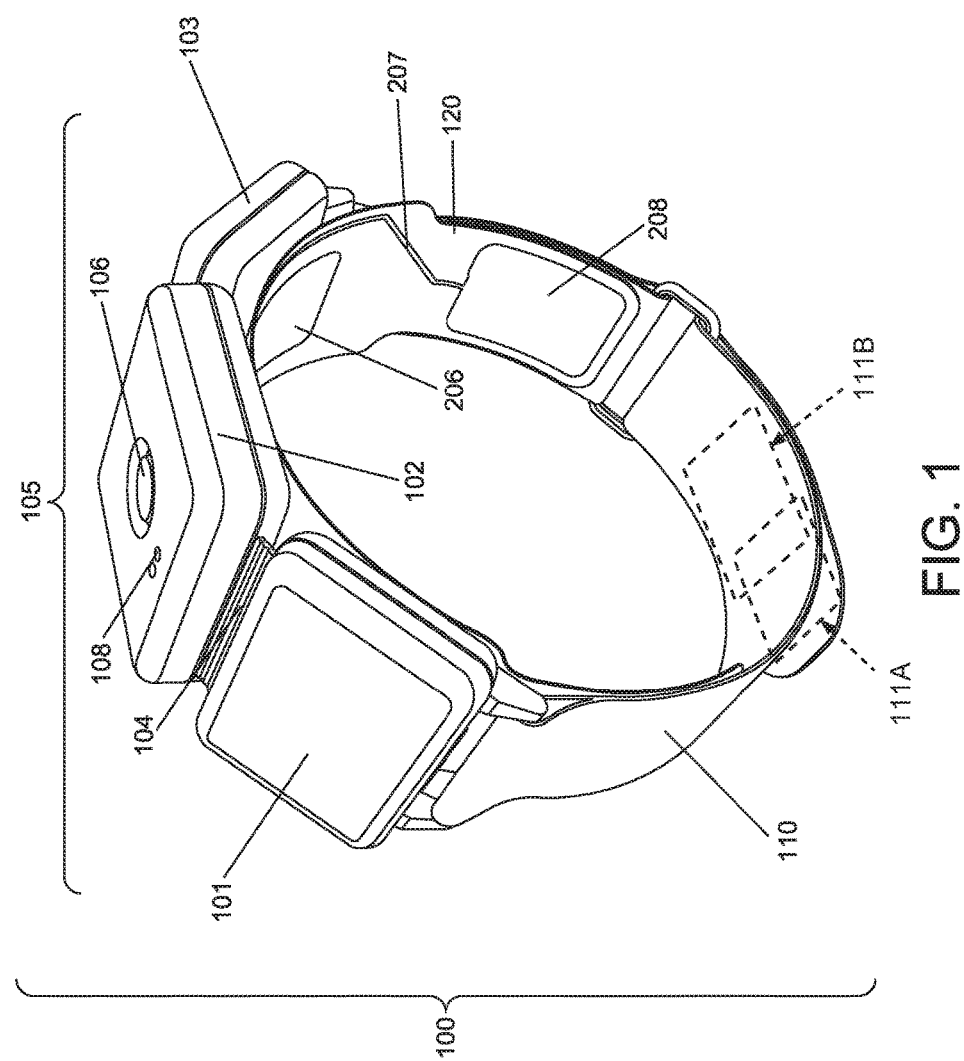
FIG. 1 is a schematic view showing a novel TENS apparatus formed in accordance with the present invention.

Looking first at FIG. 1, there is shown a novel TENS apparatus 100 which comprises one preferred form of the present invention. TENS apparatus 100 generally comprises three components: a stimulator 105, a strap 110, and an electrode array 120.

Stimulator 105 comprises three mechanically and electrically inter-connected compartments 101, 102, and 103. Compartments 101, 102, 103 are inter-connected by hinge mechanisms 104, thereby allowing TENS assembly 100 to conform to the curved anatomy of a user's leg. In the preferred embodiment, compartment 102 contains stimulation hardware (except for a battery) and user interface elements 106, 108. In the preferred embodiment, compartments 101 and 103 are smaller, auxiliary compartments that house a battery for powering the stimulation hardware and other ancillary elements.

Figure 2:
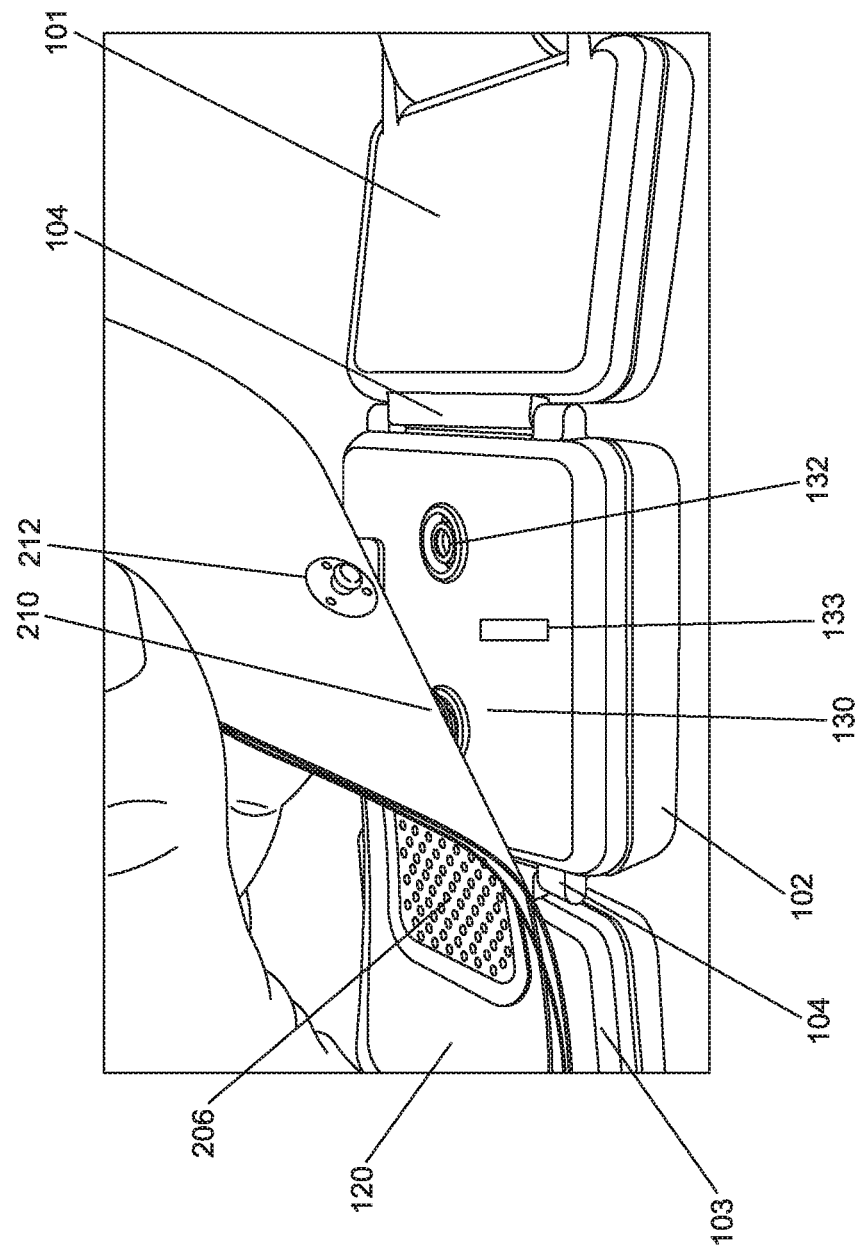
FIG. 2 is a schematic view showing an electrode array being electrically and mechanically connected to the stimulator of the TENS apparatus shown in FIG. 1.

As shown in FIG. 2, electrode array 120 comprises electrical contacts 210, 212 that snap into mating ports 130, 132 provided on the underside of central stimulator compartment 102. When snapped together, stimulator 105 and electrode array 120 are mechanically and electrically connected. This direct electro-mechanical connection between stimulator 105 and electrode array 120 eliminates the need for inconvenient lead wires found in other TENS devices.

Central stimulator compartment 102 also has a USB port 133 on its underside for (i) charging the battery contained in one of the outboard compartments 101, 103, (ii) downloading of utilization data, (iii) configuring the stimulator 105, and (iv) uploading of software upgrades. In the preferred embodiment, USB port 133 is not electrically isolated from the stimulator hardware in order to simplify the design and lower manufacturing costs. However, the location of USB port 133 on the underside of central stimulator compartment 102 prevents use of the USB port when an electrode array 120 is attached to stimulator 105, e.g., as may be understood from FIG. 2. As a result, electrical safety is maintained because stimulator 105 cannot be used to deliver stimulation to a patient via electrode array 120 while stimulator 105 is simultaneously connected to another device, e.g., a power supply, via USB port 133.

Looking again at FIG. 1, stimulator 105 includes a push button 106 for control of electrical stimulation, and LEDs 108 for indicating stimulation status and providing other feedback to the patient. Although the preferred embodiment shown in FIG. 1 comprises a single push button 106 and two LEDs 108, other constructions may also be used, e.g., two or more push buttons, etc. Additional user interface elements (e.g., an LCD display, audio feedback through a beeper or voice output, haptic devices such as a vibrating motor, etc.) have been contemplated and are considered to be within the scope of the present invention. In the preferred embodiment, main compartment 102 of stimulator 105 includes an accelerometer (not shown), preferably in the form of a semiconductor chip, to detect user gestures such as tapping (or slapping) on central compartment 102. Additional uses for the accelerometer include the detection of certain movement characteristics of TENS apparatus 100, and therefore identification of patient orientation and activity, such as lying, standing, walking, gait, etc., which permits modifying the stimulation characteristics of stimulator 105 in order to optimize stimulation for the identified patient state. In addition to the user interface elements noted above, the electrical stimulation itself can serve a user interface function. More particularly, the patient will generally recognize changes in the stimulation pattern. Thus, for example, the stimulator 105 can indicate to the patient that the stimulation intensity has reached a maximum value by pulsing stimulation on and off with a fixed on and off period (e.g., 0.5 seconds) for a short period of time (e.g., 3 seconds).

In the preferred embodiment, and still looking now at FIG. 1, the user interface elements (e.g., push button 106 and LEDs 108) are physically located on stimulator 105. In alternative embodiments, one or more of the user interface components may be remotely located. These remote user interface elements may be connected to stimulator 105 through a variety of means including a physical link such as a wire, a wireless link such as a Bluetooth® connection, an optical link such as an infra-red (IR) connection, etc. These remote user interface elements may be located on dedicated devices specifically designed to control stimulator 105 such as a custom remote control, or they may be incorporated into existing devices used by the patient such as a smart phone, a tablet computer, etc.

Figure 3:
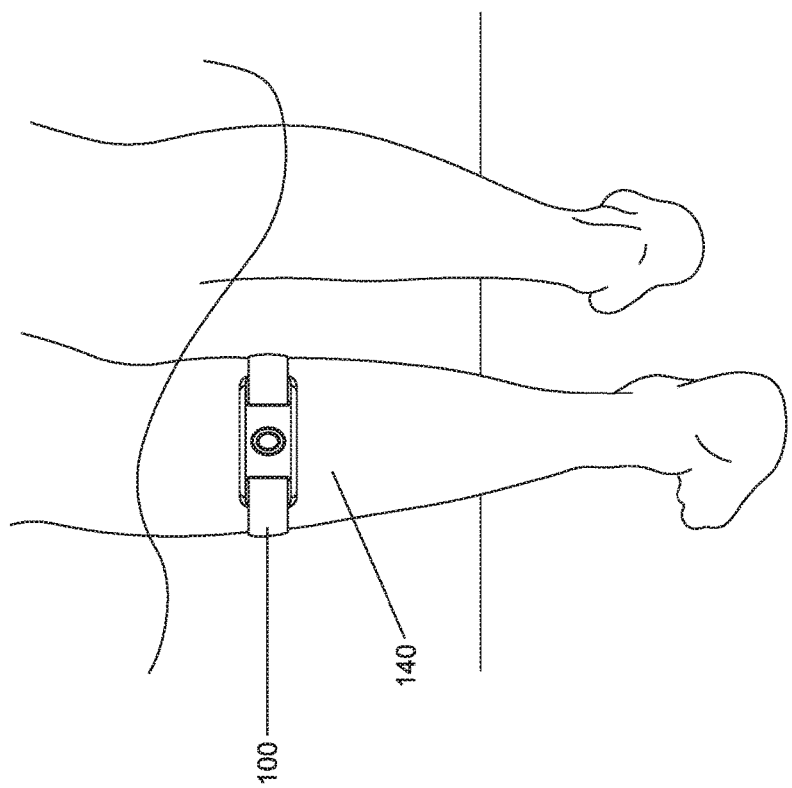
FIG. 3 is a schematic view showing the TENS apparatus of FIG. 1 mounted to the upper calf of a patient.

As seen in FIG. 3, strap 110 serves to securely and comfortably attach stimulator 105 to the patient's leg in the upper calf region 140. In the preferred embodiment, strap 110 is constructed from material that includes Velcro® which allows the device to be easily secured to a variety of different calf sizes. It is also possible to make the strap removable from stimulator 105 and thereby offer straps of varying sizes to more readily adapt to particularly small or large calves. Strap 110 may also include a mechanism (not shown), such as a clip, for holding the ends of electrode array 120 in place.

Strap 110 may also include electronic means 111A, 111B (FIG. 1) that determine calf circumference and/or other biometric data (e.g., skin temperature) and communicate this data to stimulator 105 for optimization of stimulation parameters.

The preferred embodiment of the invention is designed to be worn on the patient's upper calf 140 as shown in FIG. 3. A patient may wear a TENS apparatus 100 on one or both legs depending on the nature and level of their pain, and as directed by their physician. In the case of two TENS apparatus 100, the devices may communicate with one another through a wireless link to synchronize their operation. TENS apparatus 100, comprised of stimulator 105, electrode array 120 and strap 110, is secured to upper calf 140 by placing the apparatus in position and then tightening strap 110 so as to secure electrode array 120 against the skin of the patient. The particular rotational disposition of TENS apparatus 100 on upper calf 140 is not clinically important as the construction and operation of electrode array 120 is intentionally designed to be independent of the exact rotational position of TENS apparatus 100. More particularly, and as will hereinafter be discussed in further detail, electrode array 120 is deliberately sized and configured so that it will apply appropriate electrical stimulation to the appropriate anatomy of the patient regardless of the specific rotational position of TENS apparatus 100 on the calf of the patient.

Figure 4:
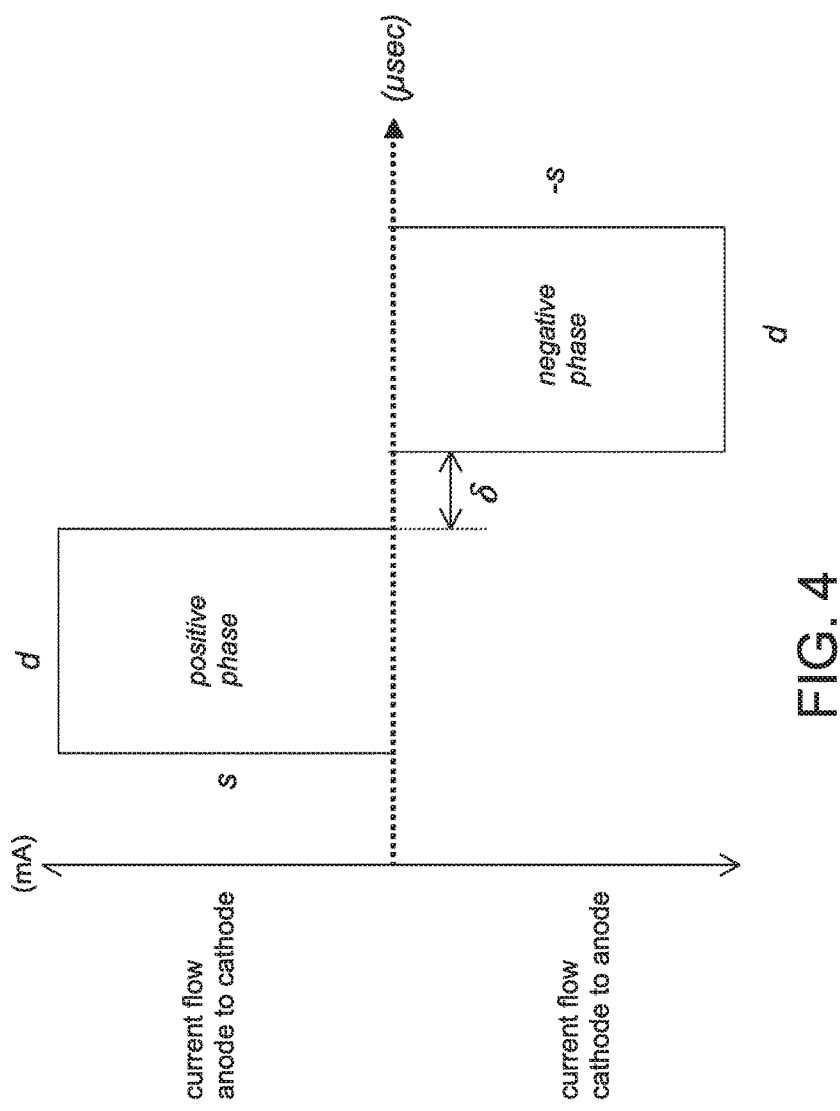
FIG. 4 is a schematic view showing the biphasic, symmetrical, rectangular pulses with regulated current generated by the stimulator of the TENS apparatus of FIG. 1.

Stimulator 105 is a microprocessor-controlled circuit which generates biphasic, symmetrical, rectangular pulses with regulated current, as shown in FIG. 4. This pulse waveform is charge-balanced which prevents iontophoretic build-up under the electrodes of the electrode array 120 that can lead to skin irritation and potential skin damage. Regulated current pulses provide more stable stimulation than regulated voltage pulses, because the stimulation current is independent of the electrode-skin impedance, which typically changes during the course of a therapy session. In order to address a wide variety of skin types and electrode quality (due to repeat use and air exposure), the maximum output voltage is 100V and the maximum output current is 100 mA. Finally, the pulse pattern is continuous stimulation with randomly varying inter-pulse intervals such that the frequency of stimulation has a uniform probability distribution between 60 Hz and 100 Hz. Alternatively, the frequency of stimulation may have a Gaussian probability distribution between 60 Hz and 100 Hz, or some other probability distribution. The benefit of providing frequency stimulation with randomly varying inter-pulse intervals (versus frequency stimulation with constant inter-pulse intervals) is that the former type of stimulation may lead to less nerve habituation, which is a physiological decrease in nerve responsiveness to stimulation. Preferably the gap between the positive and negative phases of the pulse pattern is relatively small and uniform, although the gap may be omitted, or modified, if desired. In this respect it should be appreciated that the presence of the gap between the positive and negative phases of the pulse pattern is primarily a consequence of simplified circuit design. Although the preferred embodiment of stimulator 105 has specific technical characteristics, other technical specifications (such as for the pulse waveform shape, maximum output voltage, maximum output current, and pulse pattern) have been contemplated and are considered to be within the scope of the present invention. In another embodiment, the stimulation attributes of stimulator 105 are programmable, with the stimulator being connectable (such as through the USB port) to a computer or mobile device (e.g., smart phone, tablet computer, etc.) running appropriate setup software. In this fashion, the stimulation attributes of stimulator 105 can be customized to the user's pain characteristics, physiology, and preferences.

Figure 5:
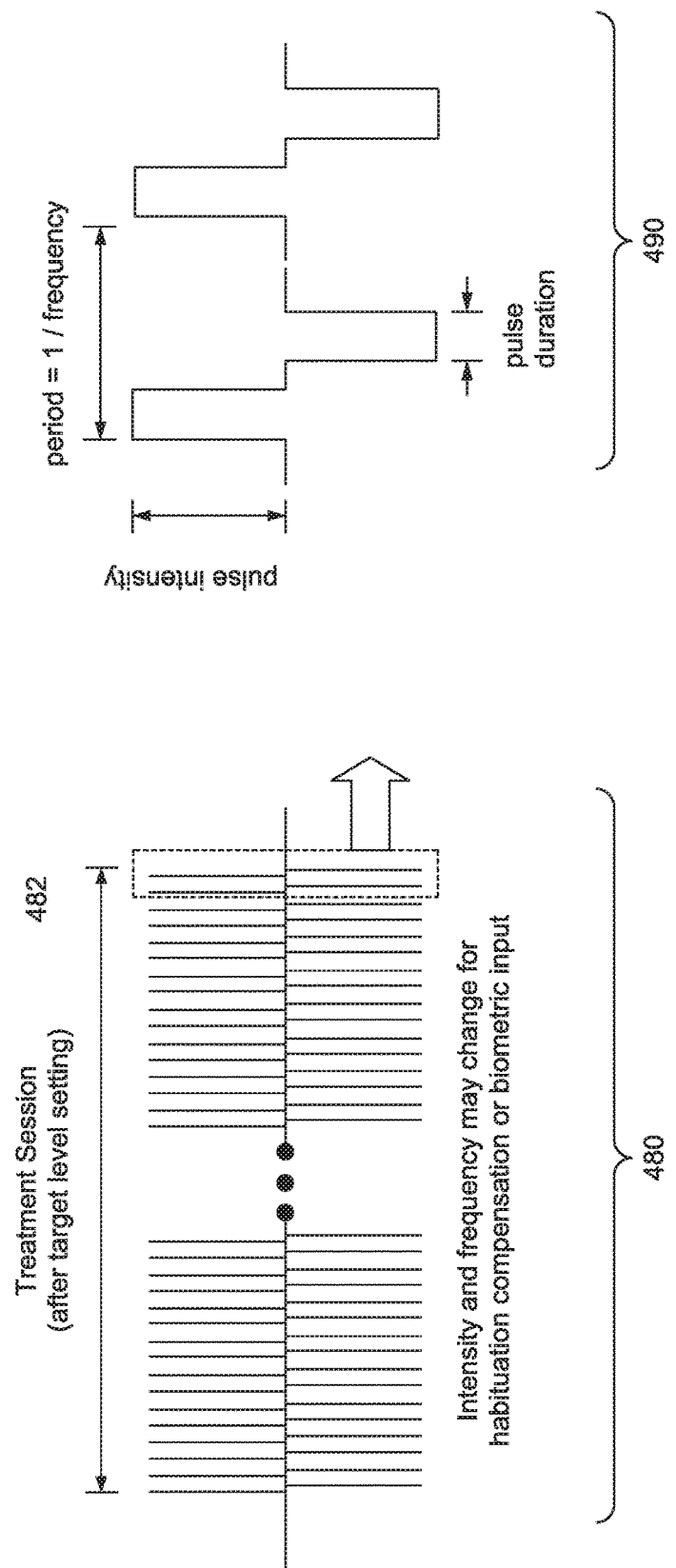
FIG. 5 is a schematic view showing the pulse train provided by the stimulator of the TENS apparatus of FIG. 1.

FIG. 5 is a schematic view of an exemplary pulse train 480 provided by stimulator 105 during a therapy session and shows the waveform of two individual pulses 490, each of which has the spaced biphasic waveform shown in FIG. 4. Pulses of fixed or randomly varying frequencies persist throughout the therapy session duration 482. The intensity of the stimulation (i.e., the amplitude of the current delivered by stimulator 105) is adjusted in response to patient input and for habituation compensation, as is described below.

Figure 6:
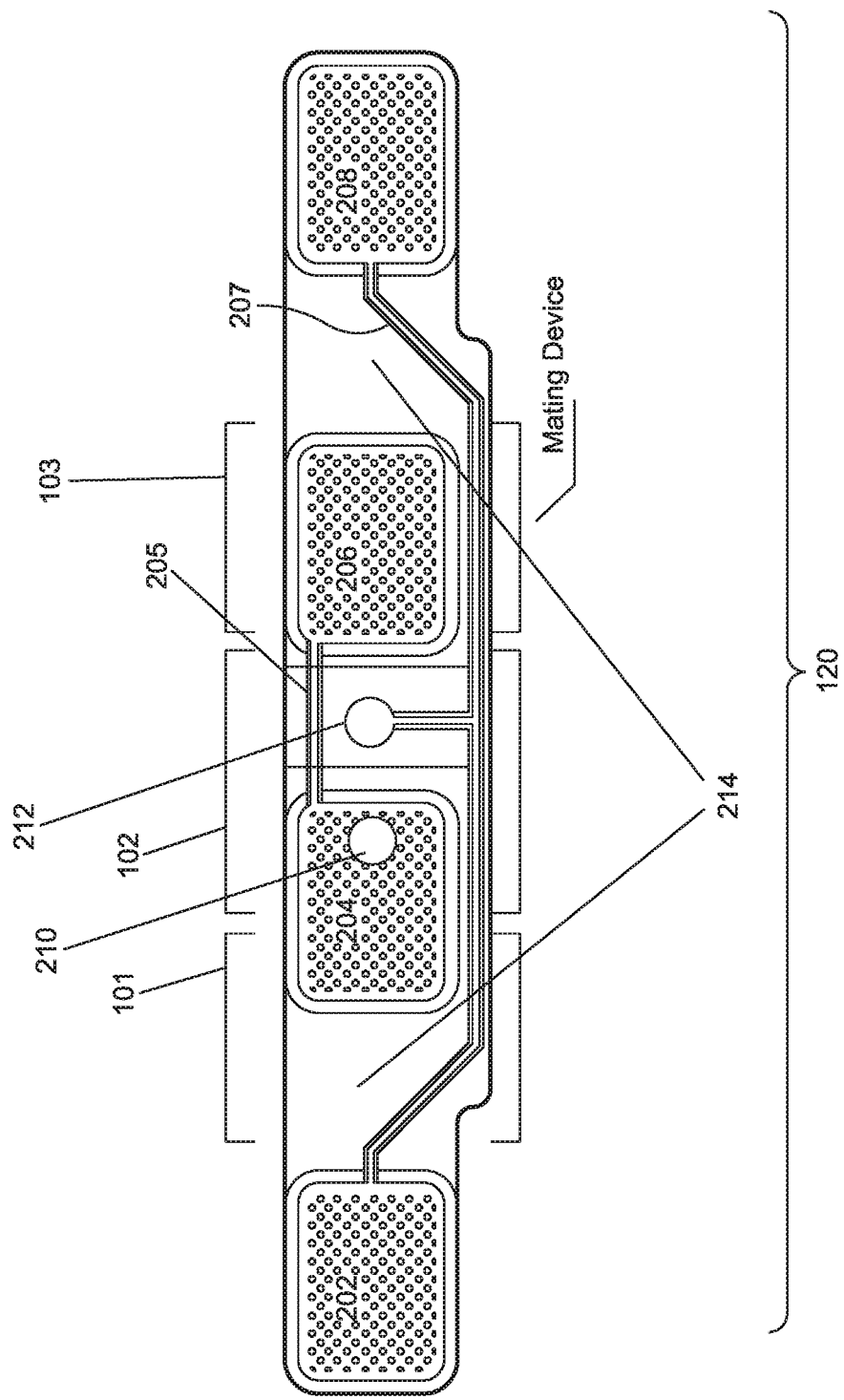
FIG. 6 is a schematic view of the underside of the electrode array of the TENS apparatus of FIG. 1.
Figure 7:
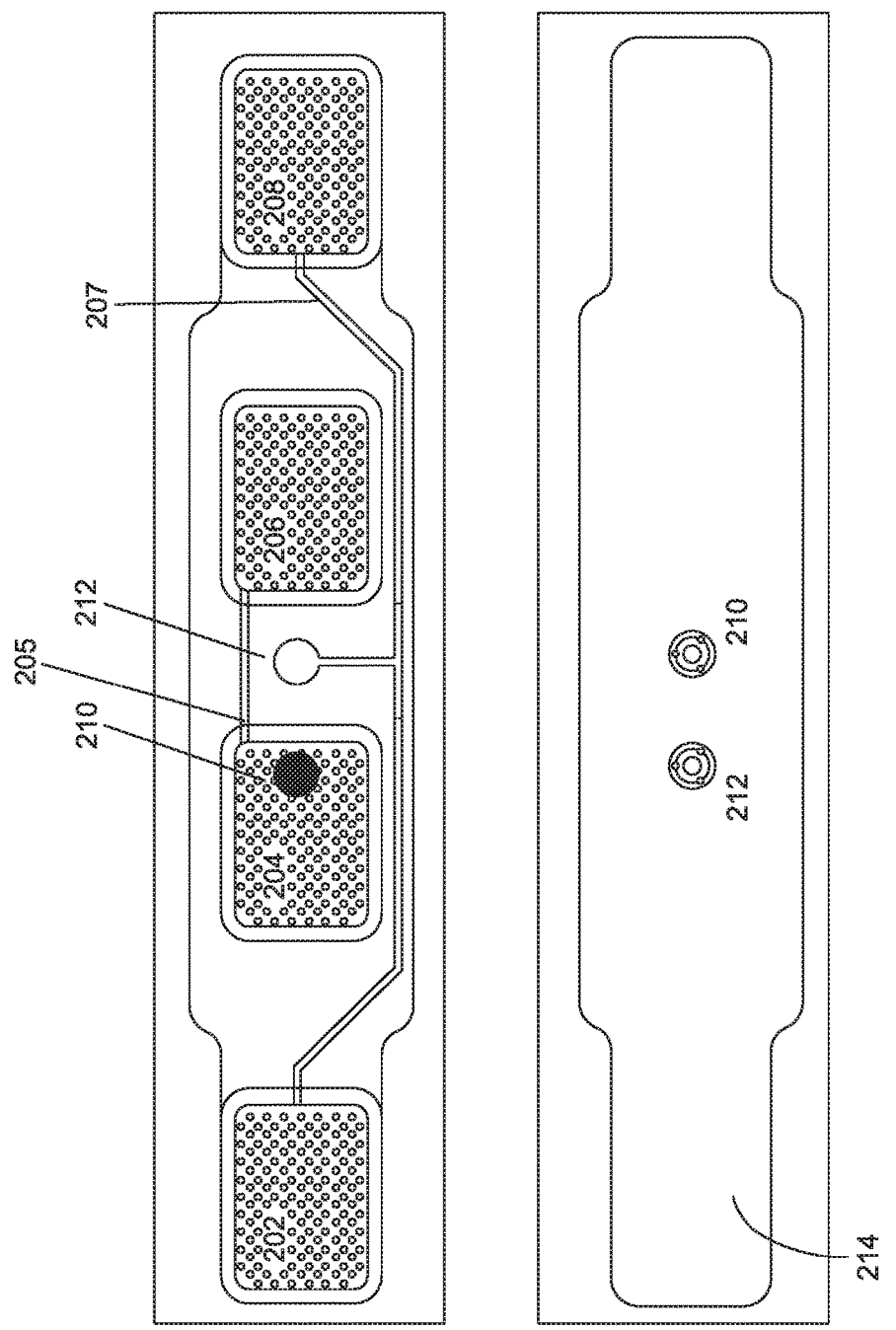
FIG. 7 is a photograph showing the top side and the underside of the electrode array of the TENS apparatus of FIG. 1.

A schematic of the preferred embodiment of electrode array 120 is shown in FIG. 6. Electrode array 120 preferably comprises four discrete electrodes 202, 204, 206, 208, preferably each electrode having an equal surface area. Electrodes 202, 204, 206, 208 are connected in pairs so that electrodes 204 and 206 (representing the cathode) are electrically connected to one another (e.g., via connector 205), and so that electrodes 202 and 208 (representing the anode) are electrically connected to one another (e.g., via connector 207). It is understood that when the polarity of the electrical pulse is reversed, the roles of the cathode and anode electrodes are also reversed. It should be appreciated that electrodes 202, 204, 206 and 208 are appropriately sized, and connected in pairs, so as to ensure adequate skin coverage regardless of the rotational position of electrode array 120 on the leg of a patient. Furthermore, it should be appreciated that electrodes 202, 204, 206 and 208 are not connected in an interleaved fashion, but rather are connected so that the two inside electrodes 204 and 206 are connected to one another, and so that the two outside electrodes 202 and 208 are connected to one another, so as to ensure that if the two outer electrodes 202 and 208 should inadvertently come into contact with one another, such as might occur in a patient with a thin calf, the electrode array will not be shorted out. Electrical current (i.e., for electrical stimulation to the tissue) is provided to the electrode pairs by connectors 210, 212 (see also FIG. 2) which mate with complementary connectors 130, 132 on stimulator 105 (see also FIG. 2). Connector 210 is electrically connected with electrodes 204 and 206, and connector 212 is electrically connected with electrodes 202 and 208. Stimulator 105 generates electrical currents that are passed through electrodes 204, 206 and electrodes 202, 208 via connectors 210, 212, respectively. The individual electrodes 202, 204, 206, 208 are preferably constructed from a hatched silver pattern overlaid with a conductive hydrogel. The backing 214 for electrode array 120 is preferably Mylar on which the aforementioned silver patterns are printed. Electrical connections between the electrodes 202, 204, 206, 208 and the connectors 210, 212 (i.e., connectors 205, 207) are formed by printed silver traces which are covered with an insulating material. Additional embodiments of electrode array 120 have been contemplated including the use of varying numbers of electrodes, different electrode sizes and different inter-electrode spacing, and alternative electrode silver patterns such as a solid, and are considered to be within the scope of the present invention.

Electrode array 120 is designed for circumferential placement around the patient's upper calf as shown in FIG. 3. The design of electrode array 120 ensures that a minimum distance is always maintained between the electrodes 204, 206 forming the cathode and the electrodes 202, 208 forming the anode. In the preferred embodiment, this minimum distance is 40 mm. In this respect it should be noted that a minimum cathode-to-anode distance is critical for proper TENS operation because if the cathode and the anode are too close to one another, the stimulation current does not penetrate sufficiently deeply into the tissue and the ability to stimulate nerves is compromised.

When stimulator 105 and electrode array 120 are connected together as shown in FIG. 2, and placed on the patient (using strap 110) as shown in FIG. 3, the individual electrodes 202, 204, 206, 208 are positioned to deliver stimulation to the L4, L5, S1 and S2 sensory dermatomes which provide sensation to the foot and lower leg. As a result, the invention is particularly suitable for providing analgesia in the foot and lower leg, which supports its preferred use for the symptomatic treatment of chronic pain due to PDN.

The use of the preferred embodiment of the present invention is straightforward. The user snaps an electrode array 120 into stimulator 105 (FIG. 2), thereby establishing a secure mechanical and electrical contact between the two components. Using strap 110, this assembly is then placed on the upper calf of the patient (FIG. 3) so that the electrodes of electrode array 120 are securely disposed against the skin of the patient. Stimulation is initiated by pressing the control push button 106. Upon completion of the therapy session, TENS apparatus 100 is removed from the patient and electrode array 120 is detached from stimulator 105. Electrode array 120 may be used multiple times on a single patient.

A major objective of the present invention is to simplify the user interface, and therefore a one-button interface is preferred. Conventional TENS devices typically have multiple user interface elements consisting of on/off switches, buttons to increase/decrease the stimulation intensity, dials to change the stimulation intensity, and other controls to regulate device function. The correct use of such prior art user interfaces requires that the patient have unfettered physical and visual access to the device, which limits placement of the device to certain anatomical locations, such as on a belt clip. By comparison, the present invention utilizes a simple one-button interface that does not require visual confirmation and is easily operated with the device placed anywhere on the body, including the lower leg as shown in FIG. 3. In the preferred embodiment of the present invention, which utilizes a one-button interface, the device is powered on (either from a low power stand-by state or from an off-state) by a button press. Stimulation intensity is controlled through short and long button presses. More particularly, holding the button down increases the stimulation intensity as long as the button is depressed, such as at the rate of 1 milliamp per second. Pressing and quickly releasing (i.e., "tapping") the button decreases the stimulation intensity by a fixed amount, such as 1 milliamp per button press or by a fixed percentage, such as 2% per button press. In this fashion, the stimulation intensity can be easily controlled by the patient with a single push button (i.e., push button 106). The present invention further discloses the provision of an accelerometer to detect user gestures such as slapping (or tapping) the stimulator enclosure 102. In the preferred embodiment, the detection of a slap immediately stops stimulation.

There is no universal TENS stimulation intensity that provides an effective, yet tolerable, therapeutic dose for all patients. Therefore, in order to obtain the clinical benefit of TENS therapy, it is essential to set the stimulation intensity to a patient-specific level. A stimulation intensity that elicits a "strong but not painful" sensation will provide effective pain relief, and is therefore suggestive of an intensity that is within the therapeutic window. The traditional approach in TENS is for the medical staff to train patients on how to manually increase the intensity of the TENS stimulation until the patients perceive the desired "strong but not painful" sensation. It is then the responsibility of the patient to thereafter perform this procedure as necessary, e.g., at home when TENS therapy is needed. However, this prior art approach requires the use of expensive medical resources (i.e., medical staff time) and is error prone inasmuch as previously-trained patients may forget how to determine an appropriate therapeutic intensity. As a result, a major objective of the present invention is to automatically and reliably set the stimulation intensity within the therapeutic range.

The present invention discloses a method for automatically setting the stimulation intensity to a therapeutic level, a procedure which is sometimes hereinafter referred to as "configuration". This method is based on the concept of mapping a patient's electrotactile perception scale, on which the "strong but not painful" sensation is represented, to an electrical stimulation intensity scale as measured in milliamps. In this respect, the term "electrotactile" is meant to refer to a patient's sensation of electrical stimulation. There are three key measurable electrotactile perception levels: electrotactile sensation threshold (i.e., the lowest level of electrical stimulation which the patient can sense), electrotactile pain threshold (i.e., the level of electrical stimulation which causes pain to the patient), and electrotactile tolerance threshold (i.e., the maximum level of electrical stimulation which can be tolerated by a patient). An optimal TENS stimulation intensity is located between the electrotactile sensation threshold and the electrotactile pain threshold.

Figure 8:
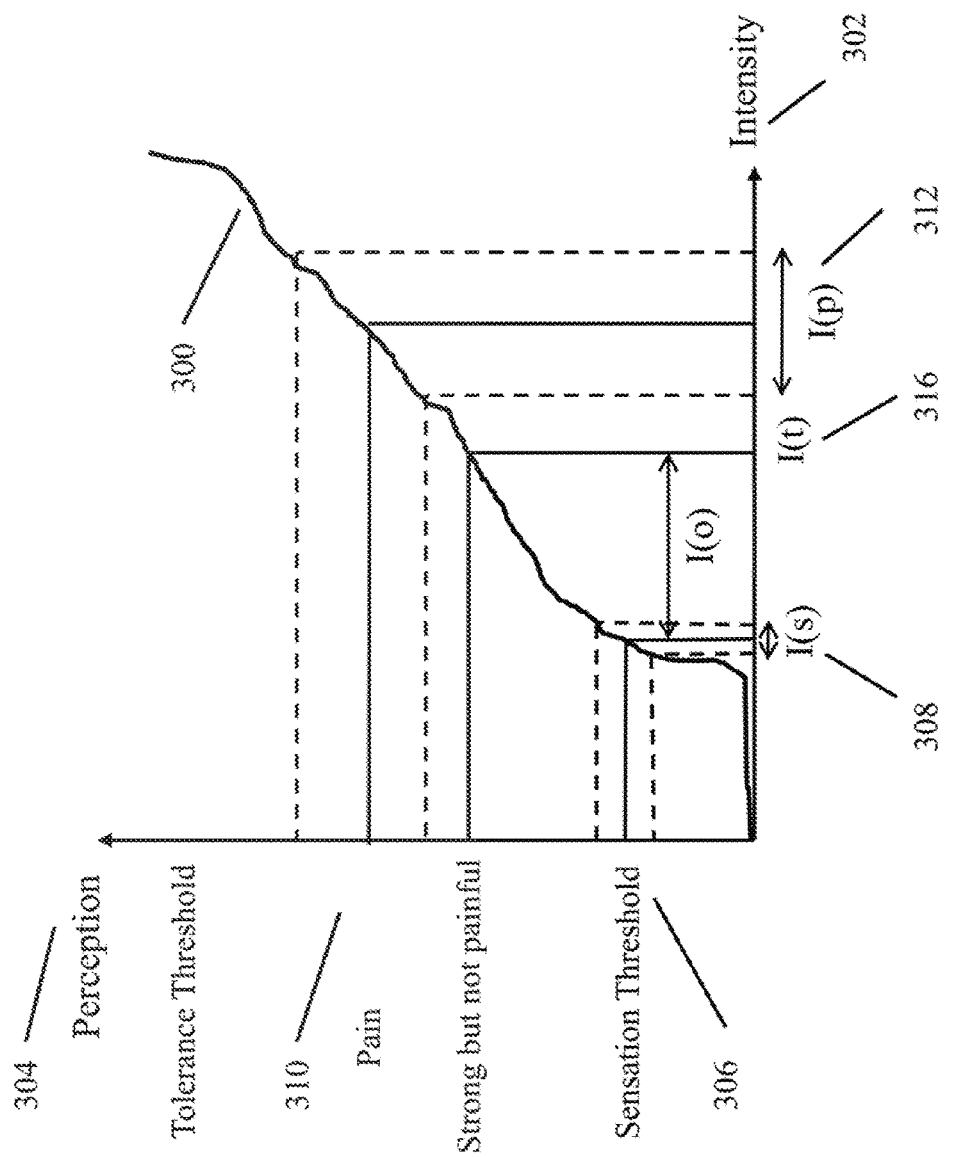
FIG. 8 is a schematic graph showing the relationship between electrotactile perception and electrical stimulation intensity.

FIG. 8 shows a curve 300 illustrating the relationship between electrical stimulation intensity 302 and electrotactile perception 304. The slope of curve 300 is steep near the electrotactile sensation threshold 306, so the range 308 of stimulation intensities, I(s), which may first elicit sensation in the patient is generally narrow. As a result, the electrotactile sensation threshold 306, and the corresponding stimulation intensity 308, i.e., I(s), can be reliably determined.

The electrotactile pain threshold 310, which is defined as the level where electrical stimulation sensation changes from comfortable to painful, is not as well-defined and is influenced by multiple physiological and psychological factors. As a result, the curve 300 is not as steep in the electrotactile pain threshold region 310 as in the electrotactile sensation threshold region 306. This can lead to a wide range 312 of stimulation intensities, I(p), at which the transition to pain occurs. For this reason, it may be difficult to reliably measure the electrotactile pain threshold 310, and the corresponding stimulation intensity 312. Another drawback with measuring the electrotactile pain threshold 310 is that it necessitates stimulation with current intensities that are at the upper limit of the patient's comfortable range and, due to the variation in the exact pain threshold 310, may occasionally be perceived as painful. Consequently, a patient may consistently underestimate his/her pain threshold, leading to a stimulation level which is below the optimal therapeutic range if the therapeutic level is estimated from the electrotactile pain threshold 310.

Since the stimulation intensity I(s) associated with the electrotactile sensation threshold 306 can be reliably estimated, a target therapeutic stimulation intensity I(t), which provides a "strong but not painful" sensation, may be calculated by adding an intensity offset I(o) to the stimulation intensity I(s) associated with the electrotactile sensation threshold. In other words, where I(s) is the stimulation intensity associated with the electrotactile sensation threshold, an intensity offset I(o) may be added to the stimulation intensity I(s) so as to determine the stimulation intensity I(t) which is "strong but not painful", i.e., therapeutically effective and yet comfortable for the patient. This is a new and innovative method for determining a stimulation intensity that is strong but not painful to the patient.

A preferred embodiment of this procedure for automatically setting the stimulation intensity to a therapeutic level is to gradually increase the stimulation intensity from 0 mA until the patient indicates that the stimulation is first felt, i.e., that the electrotactile sensation threshold has been reached, such as by using the push button 106. In a preferred embodiment, the stimulation intensity is increased in a geometric progression. For example, the stimulation intensity may increase by 5% every second (i.e., stimulation intensity is 1.05 times the prior stimulation intensity). The benefit of a geometric progression is that it better matches the exponential relationship of stimulus intensity and electrotactile sensation (i.e., the so-called "psychophysical power law") than does a linear increase in intensity (e.g., 1 mA per second). The procedure can be repeated multiple times to allow a more accurate estimate of the electrotactile sensation threshold and the associated intensity I(s), such as by taking the mean or median of multiple measurements. In a preferred embodiment, the first determination of the electrotactile sensation threshold is discarded because the patient may not be familiar with the perception of electrical stimulation and may therefore underestimate or overestimate the correct level.

An increment of stimulation intensity, i.e., an intensity offset I(o), is then added to the stimulation intensity I(s) associated with the electrotactile sensation threshold so as to estimate the therapeutic intensity, I(t), 316.

In a preferred embodiment, the stimulation intensity offset I(o) is a constant for all patients. Because sensory perception typically varies in a logarithmic fashion, the relationship between the therapeutic intensity, I(t), and the sensation threshold intensity, I(s), is expressed as a ratio (e.g., 2), or in decibels (e.g., 6 dB), where the ratio=$10^{(dB/20)}$.

In another preferred embodiment, the stimulation intensity offset I(o) varies according to manual changes in the stimulation intensity made by the patient. As an example, if, after a first determination of the therapeutic intensity (i.e., by adding a default offset I(o) to the stimulation intensity I(s) associated with the electrotactile sensation threshold 306), the patient then manually increases the stimulation intensity (as determined by the above procedure) during a subsequent therapy session, it is likely that the optimal intensity offset for that patient is larger than the default offset. Therefore, in a subsequent determination of the therapeutic intensity, a larger stimulation intensity offset is used. Similarly, if, after a first determination of the therapeutic intensity (i.e., by adding a default offset I(o) to the stimulation intensity I(s) associated with the electrotactile sensation threshold 306), the patient then manually decreases the stimulation intensity during a subsequent therapy session, it is likely that the optimal intensity offset for that patient is smaller than the default value. Therefore, in a subsequent determination of the therapeutic intensity, a smaller stimulation intensity offset is used. In this fashion, the therapeutic intensity estimated from the sensation threshold is adaptive and responsive to the patient's input.

Additional embodiments of the present invention have been contemplated wherein the stimulation intensity offset I(o) is determined as a function of demographic or biometric variables such as the gender of the patient, circumference of the calf of the patient, calf temperature, and level and type of activity (e.g., rest, sleep, walking). As an example, it is known that males have higher electrotactile thresholds than females, and therefore the stimulation intensity offset I(o) can be set to gender specific values wherein the male intensity offset is greater than the female intensity offset. As another example, a patient with a large calf is likely to require a higher stimulation intensity level than a patient with a smaller calf due to the distance between the skin and the underlying nerves which are to be stimulated. Therefore, the calf size (which, in one preferred form of the invention, may be electronically measured by the strap 120 and communicated to the stimulator 105) may be used as an input to determine the stimulation intensity offset to be used for that patient. As yet another example, it is known that electrotactile thresholds are inversely related to the temperature of the patient, which may be approximated by measuring the patient's skin surface temperature. Therefore, the stimulation intensity offset can be increased (for lower patient temperatures) or decreased (for higher patient temperatures) as a function of the skin surface temperature to address these temperature-dependent changes in electrotactile perception. The skin surface temperature can be measured with a non-contact infrared thermosensor (e.g., MLX90615, Melexis Semiconductors, Belgium) or a contact digital thermosensor (e.g., DS1820, Maxim, Inc., Sunnyvale, Calif.), which can be embedded in the strap 110 or the enclosure of stimulator 105. Although the use of skin surface temperature is described with respect to estimation of the therapeutic intensity from the sensation threshold, additional embodiments of the present invention have been contemplated in which skin surface temperature is used to continuously adjust the stimulation intensity during a therapeutic session to account for temperature changes.

Once a therapeutic intensity level I(t) is determined, TENS apparatus 100 is ready to be used for therapeutic purposes. The patient may re-establish the therapeutic intensity, i.e., I(t), from time to time. It should be noted that a TENS device can be used without automatic determination of the therapeutic intensity level by using a universal intensity level, such as a maximum safe therapeutic intensity. However, such a fixed approach is severely limited as described above.

In a preferred embodiment, when a patient initiates a treatment session, the stimulation intensity will steadily ramp up to the target intensity, I(t), 316, where the target intensity has been determined by previously conducting electrotactile perception mapping for that patient (which identified the stimulation intensity I(s) associated with the sensation threshold) and then adding the desired intensity offset I(o) so as to establish the therapeutic stimulation intensity I(t) to be used for that patient. The stimulation intensity should gradually increase to the target intensity (i.e., the therapeutic stimulation intensity) I(t) over a sufficiently long period of time such that the patient will not be surprised by the stimulation or become uncomfortable with the stimulation. In the preferred embodiment, the stimulation intensity increases to the target intensity over a time period of 1 minute, and this is done in three phases. In the first phase, the stimulation intensity increases to 90% of the sensation threshold in 5 seconds. These intensity levels are sub-sensation threshold and therefore should not be perceived by the patient. In the second phase, the stimulation intensity increases from 90% to 112% (+1 dB) of the sensation threshold in 10 seconds. These stimulation intensities are near the sensation threshold and should be minimally perceived by the patient and will not be uncomfortable. In the third and final phase, the stimulation intensity increases from 112% of the sensation threshold to the target intensity (i.e., the therapeutic stimulation intensity). This gradual increase in stimulation intensity gives the patient the opportunity to become comfortable with the stimulation and avoids startling the patient.

In the preferred embodiment, the patient may further refine the stimulation intensity by increasing or decreasing the stimulation intensity using push button 106. In a preferred embodiment, the stimulation intensity cannot be decreased below an intensity "floor" which ensures that the stimulation intensity remains in a likely therapeutic range. As an example, the intensity floor can be set to 12% (1 dB) above the sensation threshold.

A novel benefit of determining the electrotactile sensation threshold in the foregoing manner is that the likely therapeutic benefit of the stimulation intensity used by the patient, particularly if manually modified by the patient from the automatic level determined as described above, can be evaluated. In the preferred embodiment, the utilization data stored by the stimulator 105 includes the stimulation intensity of each therapy session. As such, when the utilization data is uploaded to a computer, the average therapy level for that patient can be calculated and reported as, for example, a decibel level over the sensation threshold. The patient's physician can then assess this value against the pain relief obtained by the patient and make appropriate clinical recommendations. For example, if the patient has a low therapy level (e.g., 2 dB above the sensation threshold intensity, I(s)) and the patient is not obtaining pain relief, the physician may then suggest that the patient re-establish their therapeutic intensity using the configuration procedure described above.

Habituation refers to a decrease in the sensory perception of a stimulus by the patient after the prolonged presentation of the stimulus to the patient. As applied to TENS therapy, habituation may cause a decrease in pain relief following prolonged stimulation at the same therapeutic intensity. In traditional TENS devices, patients are instructed to manually increase the stimulation intensity from time to time if their perception of the stimulation decreases. This places the onus on the patient, who is forced to repeatedly re-engage with the TENS device, or they may entirely forget to adjust the intensity of the TENS device.

Significantly, the present invention includes a method for providing automatic habituation compensation, which consists of an automatic gradual increase in the stimulation intensity over the course of a stimulation session. In the preferred embodiment, the stimulation intensity is increased geometrically with time. In other words, the stimulation intensity is multiplied by a fixed factor per unit time. For example, the stimulation intensity may be increased by the factor 1.004 for every minute of a therapy session. This equates to an approximately 27% (2 dB) increase in stimulation intensity over a 60 minute therapy session. In another embodiment, the stimulation intensity is increased by a fixed amount, such as 0.5 milliamps, for every minute of the therapy session. In another embodiment, the rate of increase is adjusted to account for manual changes in the stimulation intensity. For example, if the patient decreases the stimulation intensity in the middle of the therapy session, then the automatic rate of increase may be too high for this patient and should be decreased for subsequent therapy sessions. Similarly, if the patient increases the stimulation intensity in the middle of the therapy session, then the automatic rate of increase may be too low for this patient and should be increased for subsequent therapy sessions. In this fashion, the automatic habituation compensation is adaptive and responsive to the patient's physiology.

Figure 9:
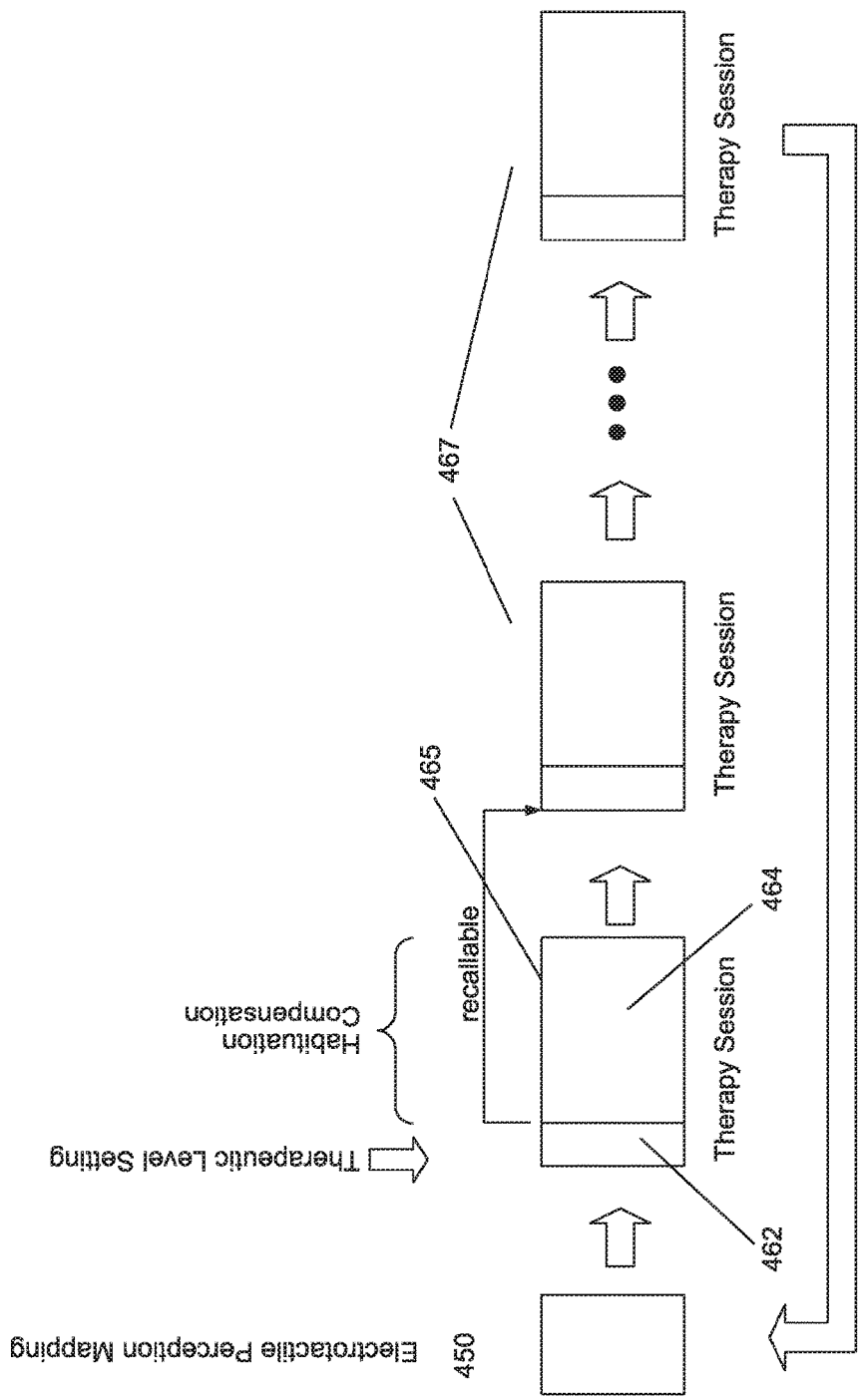
FIG. 9 is a schematic view showing the overall operation of the TENS apparatus of FIG. 1.

FIG. 9 provides an overall view of the operation of the preferred embodiment of the present invention. First, as shown at 450, the patient's electrotactile perception thresholds are mapped to stimulation intensities, i.e., the electrotactile sensation threshold is mapped to a stimulation intensity I(s), and the therapeutic stimulation intensity I(t) is determined, i.e., by adding an intensity offset I(o) to the stimulation intensity I(s). Thus, upon entering the first therapy session 465, the therapeutic intensity level has already been automatically calculated for that patient. During the first phase 462 of first therapy session 465, the patient may adjust the stimulation intensity using the user interface controls (e.g., push button 106). The stimulation intensity at the end of the this first phase 462, which typically lasts for 3 minutes, is stored and becomes the therapeutic intensity level for the next therapy session 467. Habituation compensation, as previously described, occurs throughout the rest of the therapy session (i.e., during phase 464 of first therapy session 465) and subsequent therapy sessions 467. The patient has the option of repeating the electrotactile perception mapping phase 450, which will invoke a recalculation of the therapeutic stimulation intensity I(s), after one or more therapy sessions 467.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for transcutaneous electrical nerve stimulation in humans, the apparatus comprising:
   a housing;
   stimulation means mounted within the housing for electrically stimulating nerves;
   an electrode array releasably mounted to the housing and connectable to the stimulation means, the electrode array comprising a plurality of electrodes for electrical stimulation of nerves;
   control means mounted to the housing and electrically connected to the stimulation means for controlling at least one characteristic of the stimulation means;
   monitoring means mounted to the housing and electrically connected to the stimulation means for monitoring at least one characteristic of the stimulation means;
   user interface means mounted to the housing and electrically connected to the control means for controlling the stimulation means, the user interface means comprising at least one accelerometer configured to detect a user gesture, and further wherein operation of the stimulation means is modified upon the detection of a user gesture;
   display means mounted to the housing and electrically connected to the control means and the monitoring means for displaying the status of the stimulations means; and
   a strap attached to the housing;
   wherein the strap is configured to hold the housing, stimulation means and electrode array at a specific anatomical location to treat pain.

2. Apparatus according to claim 1 wherein said anatomical location is the upper calf area of a patient.

3. Apparatus according to claim 1 wherein said pain is chronic pain.

4. Apparatus according to claim 3 wherein said chronic pain is caused by painful diabetic neuropathy.

5. Apparatus according to claim 1 wherein the housing comprises at least one compartment.

6. Apparatus according to claim 5 wherein the housing comprises a plurality of compartments which are mechanically connected by hinged means so as to allow conforming placement of the housing on a curved portion of human anatomy.

7. Apparatus according to claim 5 wherein the housing comprises a plurality of compartments which are electrically connected so as to allow physical distribution of electrical components.

8. Apparatus according to claim 7 wherein one compartment contains a stimulation circuit of the stimulation means and a second compartment contains a battery that supplies power to the stimulation circuit.

9. Apparatus according to claim 1 wherein the housing contains an interface port for connection to external devices.

10. Apparatus according to claim 9 wherein the interface port is located on the side of the housing facing the anatomy to be stimulated.

11. Apparatus according to claim 10 wherein the interface port is not accessible when the housing is positioned on the patient.

12. Apparatus according to claim 10 wherein the interface port is covered by the electrode array when the apparatus is electrically stimulating nerves.

13. Apparatus according to claim 9 wherein the interface port is a USB port.

14. Apparatus according to claim 1 wherein the stimulation means generates continuous electrical pulses.

15. Apparatus according to claim 14 wherein the stimulation means has a maximum output voltage of 100 volts.

16. Apparatus according to claim 14 wherein the stimulation means has a maximum output current of 100 milliamps.

17. Apparatus according to claim 14 wherein the electrical pulses are current regulated.

18. Apparatus according to claim 14 wherein the electrical pulses are voltage regulated.

19. Apparatus according to claim 14 wherein the electrical pulses have a symmetrical, biphasic and rectangular shape.

20. Apparatus according to claim 19 wherein the two phases of the electrical pulse are charge balanced.

21. Apparatus according to claim 19 wherein each phase of the electrical pulse has a duration of 100 microseconds.

22. Apparatus according to claim 19 wherein there is a 30 microsecond delay between the first and second phases of the electrical pulse.

23. Apparatus according to claim 14 wherein the electrical pulses have a fixed occurrence frequency.

24. Apparatus according to claim 14 wherein the electrical pulses have an occurrence frequency that varies randomly.

25. Apparatus according to claim 24 wherein the frequency varies randomly between 60 and 100 Hz with a uniform distribution.

26. Apparatus according to claim 1 wherein the at least one characteristic of the stimulation means controlled by the control means includes stimulation intensity.

27. Apparatus according to claim 1 wherein the at least one characteristic of the stimulation means controlled by the control means includes the duration of the stimulation session.

28. Apparatus according to claim 27 wherein the duration of the stimulation session is 60 minutes.

29. Apparatus according to claim 1 wherein the at least one characteristic of the stimulation means monitored by the monitoring means includes the stimulation current passing through the electrodes of the electrode array during an electrical pulse.

30. Apparatus according to claim 1 wherein the at least one characteristic of the stimulation means monitored by the monitoring means includes the voltage at the electrodes serving as the cathode of the electrode array before, during, and after an electrical pulse.

31. Apparatus according to claim 1 wherein the at least one characteristic of the stimulation means monitored by the monitoring means includes the voltage at the electrodes serving as the anode of the electrode array before, during, and after an electrical pulse.

32. Apparatus according to claim 1 wherein the at least one characteristic of the stimulation means monitored by the monitoring means includes the bioimpedance of the electrodes serving as the cathode and anode of the electrode array during an electrical pulse.

33. Apparatus according to claim 1 wherein the at least one characteristic of the stimulation means monitored by the monitoring means includes the charge passed through the electrodes of the electrode array during an electrical pulse.

34. Apparatus according to claim 1 wherein the user interface means includes a push button.

35. Apparatus according to claim 34 wherein pressing and holding the push button increases the stimulation intensity as long as the push button is depressed.

36. Apparatus according to claim 35 wherein the stimulation intensity is increased at the rate of 1 milliamp per second.

37. Apparatus according to claim 34 wherein pressing and quickly releasing the push button decreases the stimulation intensity by a fixed amount.

38. Apparatus according to claim 37 wherein stimulation is decreased by 1 milliamp per push button press.

39. Apparatus according to claim 1 wherein a detected patient gesture is a tap to the housing.

40. Apparatus according to claim 39 wherein a tap to the housing immediately stops stimulation.

41. Apparatus according to claim 1 wherein the at least one accelerometer detects orientation of the housing.

42. Apparatus according to claim 41 wherein detected orientation of the housing modifies at least one characteristic of the stimulation means.

43. Apparatus according to claim 1 wherein the at least one accelerometer detects activity level of a patient wearing the housing.

44. Apparatus according to claim 43 wherein the detected activity level modifies at least one characteristic of the stimulation means.

45. Apparatus according to claim 1 wherein the display means comprises at least one LED.

46. Apparatus according to claim 45 wherein the at least one LED indicates that stimulation is ongoing.

47. Apparatus according to claim 45 wherein the at least one LED indicates that stimulation has halted.

48. Apparatus according to claim 45 wherein the at least one LED indicates battery charging status.

49. Apparatus according to claim 1 wherein the strap is configured so that the housing can be attached to calves of different sizes.

50. Apparatus according to claim 1 wherein the strap uses Velcro® to hold the strap at the desired circumference.

51. Apparatus according to claim 1 wherein the strap is replaceable.

52. Apparatus according to claim 51 wherein the strap is selected from a group of different strap sizes so as to accommodate calves of varying sizes.

53. Apparatus according to claim 1 wherein the housing includes a mechanism to assist in stabilizing the electrode array.

54. Apparatus according to claim 1 wherein the strap includes electronic means to measure calf circumference.

55. Apparatus according to claim 54 wherein calf circumference as measured by the strap is communicated to the control means.

56. Apparatus according to claim 55 wherein the at least one characteristic of the stimulation means is modified according to calf circumference.

57. Apparatus according to claim 56 wherein stimulation intensity is modified according to calf circumference.

58. Apparatus for transcutaneous electrical nerve stimulation in humans, the apparatus comprising:
a housing;
stimulation means mounted within the housing for electrically stimulating nerves;
an electrode array releasably mounted to the housing and connectable to the stimulation means, the electrode array comprising a plurality of electrodes for electrical stimulation of nerves;
control means mounted to the housing and electrically connected to the stimulation means for controlling at least one characteristic of the stimulation means;
monitoring means mounted to the housing and electrically connected to the stimulation means for monitoring at least one characteristic of the stimulation means;
user interface means mounted to the housing and electrically connected to the control means for controlling the stimulation means, the user interface means comprising at least one accelerometer configured to detect the activity level of the patient wearing the housing, and further wherein the detected activity level modifies at least one characteristic of the stimulation means;
display means mounted to the housing and electrically connected to the control means and the monitoring means for displaying the status of the stimulations means; and
a strap attached to the housing;
wherein the strap is configured to hold the housing, stimulation means and electrode array at a specific anatomical location to treat pain.

59. Apparatus for transcutaneous electrical nerve stimulation in humans, the apparatus comprising:
a housing;
stimulation means mounted within the housing for electrically stimulating nerves;
an electrode array releasably mounted to the housing and connectable to the stimulation means, the electrode array comprising a plurality of electrodes for electrical stimulation of nerves;
control means mounted to the housing and electrically connected to the stimulation means for controlling at least one characteristic of the stimulation means;
monitoring means mounted to the housing and electrically connected to the stimulation means for monitoring at least one characteristic of the stimulation means;
user interface means mounted to the housing and electrically connected to the control means for controlling the stimulation means, the user interface means comprising at least one accelerometer configured to detect the orientation of the housing, and further wherein the detected orientation of the housing modifies at least one characteristic of the stimulation means;
display means mounted to the housing and electrically connected to the control means and the monitoring means for displaying the status of the stimulations means; and
a strap attached to the housing;
wherein the strap is configured to hold the housing, stimulation means and electrode array at a specific anatomical location to treat pain.

60. Apparatus for applying transcutaneous electrical nerve stimulation (TENS) therapy to a human, the apparatus comprising:
a housing;
an electrical stimulator mounted to the housing for generating biphasic electrical pulses of the type useful in TENS therapy;
an electrode array mountable to the housing and connectable to the electrical stimulator, the electrode array comprising a plurality of electrodes for applying the biphasic electrical pulses to a human so as to apply TENS therapy to the human; and
at least one accelerometer mounted to the housing and configured to detect a user gesture and, upon detection of a user gesture, permitting modification of the operation of the electrical stimulator.

61. Apparatus according to claim 60 wherein the user gesture is a tap.

62. Apparatus for applying transcutaneous electrical nerve stimulation (TENS) therapy to a human, the apparatus comprising:
- a housing;
- an electrical stimulator mounted to the housing for generating biphasic electrical pulses of the type useful in TENS therapy;
- an electrode array mountable to the housing and connectable to the electrical stimulator, the electrode array comprising a plurality of electrodes for applying the biphasic electrical pulses to a human so as to apply TENS therapy to the human;
- at least one accelerometer mounted to the housing and configured to detect the activity level over a period of time of the human to which the housing is secured and, depending upon the detected activity level, permitting modification of the operation of the electrical stimulator; and
- a strap attached to the housing, wherein the strap is configured to hold the housing, the electrical stimulator and the electrode array at a specific anatomical location on a limb of a human so as to apply TENS therapy.

63. Apparatus for applying transcutaneous electrical nerve stimulation (TENS) therapy to a human, the apparatus comprising:
- a housing;
- an electrical stimulator mounted to the housing for generating biphasic electrical pulses of the type useful in TENS therapy;
- an electrode array mountable to the housing and connectable to the electrical stimulator, the electrode array comprising a plurality of electrodes for applying the biphasic electrical pulses to a human so as to apply TENS therapy to the human;
- at least one accelerometer mounted to the housing and configured to detect the orientation of the housing and, depending upon the detected orientation of the housing, permitting modification of the operation of the electrical stimulator; and
- a strap attached to the housing, wherein the strap is configured to hold the housing, the electrical stimulator and the electrode array at a specific anatomical location on a limb of a human so as to apply TENS therapy.

* * * * *